United States Patent
Vincent et al.

(10) Patent No.: US 10,729,828 B2
(45) Date of Patent: *Aug. 4, 2020

(54) CLOSED DISPOSABLE MULTIPLE STERILE BLOOD BAG SYSTEM FOR FRACTIONATING BLOOD WITH THE CORRESPONDING METHOD

(71) Applicant: AENITIS TECHNOLOGIES, Mitry-Mory (FR)

(72) Inventors: Emmanuel Vincent, Mitry-Mory (FR); Pierre Bohec, Saint-Denis (FR); Jeremie Gachelin, Arcueil (FR)

(73) Assignee: AENITIS TECHNOLOGIES, Mitry-Mory (FR)

( * ) Notice: Subject to any disclaimer, the term of this patent is extended or adjusted under 35 U.S.C. 154(b) by 156 days.

This patent is subject to a terminal disclaimer.

(21) Appl. No.: 15/571,990

(22) PCT Filed: May 4, 2016

(86) PCT No.: PCT/EP2016/060090
§ 371 (c)(1),
(2) Date: Nov. 6, 2017

(87) PCT Pub. No.: WO2016/177832
PCT Pub. Date: Nov. 10, 2016

(65) Prior Publication Data
US 2018/0140758 A1 May 24, 2018

(30) Foreign Application Priority Data
May 7, 2015 (EP) .................................... 15166846

(51) Int. Cl.
*B01D 21/28* (2006.01)
*A61M 1/02* (2006.01)
(Continued)

(52) U.S. Cl.
CPC .............. *A61M 1/0281* (2013.01); *A61J 1/10* (2013.01); *A61M 1/0209* (2013.01);
(Continued)

(58) Field of Classification Search
CPC ................ A61M 1/3678; A61M 1/365; A61M 2205/3673; B01D 21/283; B01D 57/02;
(Continued)

(56) References Cited

U.S. PATENT DOCUMENTS 5,100,564 A * 3/1992 Pall ..................... A61M 1/3633
210/295
2008/0181828 A1 7/2008 Kluck
(Continued)

FOREIGN PATENT DOCUMENTS

| CN | 103906496 A | 7/2014 |
| JP | 2008-173569 A | 7/2008 |
| WO | 2013/049623 A1 | 4/2013 |

OTHER PUBLICATIONS

International Search Report, dated Jun. 6, 2016, from corresponding PCT/EP2016/060090 application.

*Primary Examiner* — Walter D. Griffin
*Assistant Examiner* — Cameron J Allen
(74) *Attorney, Agent, or Firm* — Young & Thompson

(57) ABSTRACT

Disclosed is a multiple bag system for fractionating blood, the system including a fluid collecting bag including at least one outlet port; at least first and second sampling bags, each including at least one inlet port and at least one outlet port; and a fluid transfer unit to transfer fluid from the collecting bag to the sampling bags. The fluid transfer unit includes an acoustic sorter. Also disclosed is a method for fractionating blood into blood products.

14 Claims, 6 Drawing Sheets

(51) Int. Cl.
*A61M 1/36* (2006.01)
*A61J 1/10* (2006.01)

(52) U.S. Cl.
CPC ........ *A61M 1/0236* (2014.02); *A61M 1/3678* (2014.02); *B01D 21/283* (2013.01); *A61M 1/3693* (2013.01)

(58) Field of Classification Search
CPC .... B01D 17/00; B01D 17/12; G01N 15/1404; G01N 21/453; G01N 2015/142; G01N 21/00; G01N 1/4077; G01N 2015/0288
See application file for complete search history.

(56) References Cited

U.S. PATENT DOCUMENTS

| | | |
|---|---|---|
| 2010/0078384 A1 | 4/2010 | Yang |
| 2013/0277316 A1* | 10/2013 | Dutra .................. A61M 1/3681 210/748.02 |
| 2014/0228709 A1* | 8/2014 | Hayakawa ....... A61B 5/150366 600/573 |
| 2014/0230912 A1 | 8/2014 | Aider et al. |
| 2015/0110763 A1* | 4/2015 | Leach ................. A61L 33/0094 424/93.73 |

* cited by examiner

CLOSED DISPOSABLE MULTIPLE STERILE BLOOD BAG SYSTEM FOR FRACTIONATING BLOOD WITH THE CORRESPONDING METHOD

FIELD OF INVENTION

The present invention relates to the field of blood collection and fractionation. Especially the present invention relates to a multiple blood bag system comprising an acoustic sorter for fractionating whole blood into its components. The present invention also relates to a method for preparing all kinds of blood products using a multiple blood bag system.

BACKGROUND OF INVENTION

Such blood bag system for fractionating blood usually consists of a first collecting bag used for collecting whole blood and one or more sub-bags used for fractionating blood into separated blood products. Plastic tubing couples said bags together to form a so-called closed multiple blood bag system. Typical system comprises four or five blood bags in fluid communication such that once whole blood is introduced into the system, the whole blood or its components may be moved from one bag to another by external manipulation of valves, and the like, thereby avoiding contamination. Depending on the configuration, the blood bag system may also include a white blood cells removing filter, downstream the whole blood bag.

In a typical multiple blood bag system application, whole blood is collected into a first bag and all connected blood bags, which are usually empty, are placed in a centrifuge. The bag contents are then centrifuged to separate whole bloods into its components (see FIG. 1A). By manipulating a valve, which is typically a frangible valve within the system, the blood products of the whole blood may then be transferred into one of the others blood bags, possibly for further processing. Said blood products may be red blood cell concentrate (hereinafter referred to as RBC), platelet concentrate (hereinafter referred to as PC), blood plasma (hereinafter referred to as BP) including category 1 and category 2 blood plasma, or the like.

Centrifugation of whole blood in typical blood processing raises several issues. The high rotation speed allows stratification of the whole blood (see FIG. 1B) but also induce strong shear on the cells thereby activating PC. Due to centrifugation of the whole blood, between 20 to 40% of the platelets collected may indeed be activated. It strongly affects the efficiency of the PC when injected to a patient and also reduce its storage time to no more than 5 days. Other blood products, such as RBC, may also be affected by the high rotation speed. Furthermore, fractionation of whole blood by centrifugation lasts up to 7 hours and requires several manuals steps and at least two centrifugations.

The present invention aims at overcoming the drawbacks of the prior art by providing a method for preparing all kinds of blood products and an easy-to-use, closed, disposable, sterile, multiple blood bag system enabling production of all the blood products within a single system, limiting manual operations and also avoiding any centrifugation step.

Definitions

In the present invention, the following terms have the following meanings:

"About" preceding a figure means plus or minus 10% of the value of said figure.

"Blood products" refer to specific components obtained from whole blood collected from a donor; said specific components may be red blood cell concentrate, white blood cell concentrate, blood plasma or platelet concentrate.

"Closed system" refers to a system that is isolated from its surroundings by boundaries that admits no transfer of matter across it.

"Disposable system" refers to a system configured to be thrown away after a single use.

"Sterile system" refers to an aseptic system free from living germs or microorganisms.

"Platelets activation" refers to a series of cascading responses which allow blood platelets to react to an injury by shape change, adhesiveness, aggregation, and release reaction. Blood plasma increases platelets activation.

DETAILED DESCRIPTION

The following detailed description will be better understood when read in conjunction with the drawings.

The present invention relates to a method for high throughput preparation of blood products.

The present invention especially relates to a method for high throughput preparation of blood products to be used for blood transfusion comprising the following steps:

providing a closed disposable sterile multiple blood bag system comprising:
  a fluid collecting bag B.00 comprising at least one outlet port, said fluid collecting bag containing whole blood obtained from an individual;
  first and second sampling bags B.10, B.12, each comprising at least one inlet port and at least one outlet port;
  first means for transferring fluid AS0 from the first collecting bag B.00 to the sampling bags B.10, B.12, wherein the first means for transferring fluid AS0 comprises:
    a channel extending along a longitudinal axis, the channel having a cross section with a width measured along a first transverse axis and a thickness measured along a second transverse axis (z) perpendicular to the first transverse axis, the width being greater than or equal to the thickness, the channel having first and second walls along the second transverse axis (z);
    at least one inlet in fluid communication with the channel;
    at least first and second outlets in fluid communication with the channel, the first outlet being separated, on the second transverse axis (z), from the second outlet; and
    at least one acoustic wave generator for generating acoustic wave having a wavelength within the channel;
  wherein the thickness of the channel is equal to 2l2; the at least one outlet port of the fluid collecting bag B.00 is sterilely and fluidly connected to the at least one inlet of the first means for transferring fluid AS0 and the at least first and second outlets of the first means for transferring fluid AS0 are sterilely and fluidly connected to the at least one inlet port of respectively the first and second sampling bags B.12, B.10;

applying acoustic field inside the channel of the means for transferring fluid AS0 by means of the acoustic wave generator;

transferring the content of the fluid collecting bag B.00 in the first means for transferring fluid AS0; and collecting blood cells in the first sampling bag B.10 and blood plasma in the second sampling bag B.12.

According to one embodiment, the closed disposable sterile multiple blood bag system further comprises a first buffer bag comprising at least one outlet port, said first buffer bag containing a buffer medium, and said at least one outlet port is sterilely and fluidly connected to the at least one inlet of the first means for transferring fluid AS0. According to said embodiment, the method comprises the step of transferring the content of the fluid collecting bag B.00 and the first buffer bag in the first means for transferring fluid AS0.

According to a further embodiment, the method further comprises fractionation of blood cells into platelet concentrate and red blood cell concentrate. According to said embodiment, the closed disposable sterile multiple blood bag system further comprises:

a second buffer bag B.11 comprising at least one outlet port; said second buffer bag B.11 containing a buffer medium;

third and fourth sampling bags B.20, B.22, each comprising at least one inlet port and at least one outlet port;

second means for transferring fluid AS1 from the first sampling bag B.10 to the third and fourth sampling bags B.20, B.22, wherein the second means for transferring fluid AS1 comprises:

a channel extending along a longitudinal axis, the channel having a cross section with a width measured along a first transverse axis and a thickness measured along a second transverse axis (z) perpendicular to the first transverse axis, the width being greater than or equal to the thickness, the channel having first and second walls along the second transverse axis (z);

at least one inlet in fluid communication with the channel;

at least first and second outlets in fluid communication with the channel, the first outlet being separated, on the second transverse axis (z), from the second outlet; and at least one acoustic wave generator for generating acoustic wave having a wavelength λ within the channel;

wherein the thickness of the channel is equal to λ/2; the at least one outlet port of the first sampling bag B.10 is fluidly and sterilely connected to the at least one inlet of the second means for transferring fluid AS1, the at least first and second outlets of the second means for transferring fluid AS1 are fluidly and sterilely connected to the inlet port of respectively the third and fourth sampling bags B.20, B.22, and the at least one outlet port of the second buffer bag B.11 is fluidly and sterilely connected to the at least one inlet of the second means for transferring fluid AS1.

According to said embodiment, the method further comprises the following steps:

applying acoustic field inside the channel of the second means for transferring fluid AS1 by means of the acoustic wave generator;

transferring the content of the first sampling bag B.10 and the second buffer bag B.11 in the second means for transferring fluid AS1; and collecting red blood cell concentrate in the third sampling bag B.20 and platelet concentrate in the fourth collecting bag B.22.

According to one embodiment, the white blood cells are removed using a white blood cells removing filter located between the first outlet port of the second means for transferring fluid AS1 and the at least one inlet port of the third sampling bag B.20.

According to one embodiment wherein white blood cells removing filter is not implemented, the third sampling bag B.20 comprises red blood cell concentrate and white blood cell concentrate. According to said embodiment, the content of the third sampling bag may be fractionated into red blood cell concentrate and white blood cell concentrate. According to said embodiment, the closed disposable sterile multiple blood bag system further comprises:

a third buffer bag B.21 comprising at least one outlet port; said third buffer bag B.21 containing a buffer medium;

fifth and sixth sampling bags B.30, B.31, each comprising at least one inlet port and at least one outlet port;

third means for transferring fluid AS2 from the third sampling bag B.20 to the fifth and sixth sampling bags B.30, B.31, wherein the third means for transferring fluid AS2 comprise:

a channel extending along a longitudinal axis, the channel having a cross section with a width measured along a first transverse axis and a thickness measured along a second transverse axis (z) perpendicular to the first transverse axis, the width being greater than or equal to the thickness, the channel having first and second walls along the second transverse axis (z);

at least one inlet in fluid communication with the channel;

at least first and second outlets in fluid communication with the channel, the first outlet being separated, on the second transverse axis (z), from the second outlet; and at least one acoustic wave generator for generating acoustic wave having a wavelength λ within the channel;

wherein the thickness of the channel is equal to λ/2; the at least one outlet port of the third sampling bag B.20 is fluidly and sterilely connected to the at least one inlet of the third means for transferring fluid AS2, the at least first and second outlets of the third means for transferring fluid AS2 are fluidly and sterilely connected to the inlet port of respectively the fifth and sixth sampling bags B.30, B.31, and the outlet of the third buffer bag is fluidly and sterilely connected to the at least one inlet of the third means for transferring fluid AS2.

According to said embodiment, the method further comprises the following steps:

applying acoustic field inside the channel of the third means for transferring fluid AS2 by means of the acoustic wave generator;

transferring the content of the third sampling bag B.20 and the third buffer bag B.21 in the third means for transferring fluid AS2; and collecting red blood cell concentrate in the fifth sampling bag B.30 and white blood cell concentrate in the sixth collecting bag B.31.

According to one embodiment, the platelet concentrate contains in the fourth sampling bag B.22 may be further concentrated. According to said embodiment, the closed disposable sterile multiple blood bag system further comprises:

a fourth buffer bag B.23 comprising at least one outlet port; said fourth buffer bag B.23 containing a buffer medium;

seventh and eight sampling bags B.32, B.33, each comprising at least one inlet port and at least one outlet port;

fourth means for transferring fluid AS3 from the fourth sampling bag B.22 to the seventh and eight sampling bags B.32, B.33, wherein the means for transferring fluid AS3 comprises:
  a channel extending along a longitudinal axis, the channel having a cross section with a width measured along a first transverse axis and a thickness measured along a second transverse axis (z) perpendicular to the first transverse axis, the width being greater than or equal to the thickness, the channel having first and second walls along the second transverse axis (z);
  at least one inlet in fluid communication with the channel;
  at least first and second outlets in fluid communication with the channel, the first outlet being separated, on the second transverse axis (z), from the second outlet; and
  at least one acoustic wave generator for generating acoustic wave having a wavelength $\lambda$ within the channel;

wherein the thickness of the channel is equal to $\lambda/2$; the at least one outlet port of the fourth sampling bag B.22 is fluidly and sterilely connected to the at least one inlet of the fourth means for transferring fluid AS3, the at least first and second outlets of the fourth means for transferring fluid AS3 are fluidly and sterilely connected to the inlet port of respectively the seventh and eight sampling bags B.32, B.33, and the outlet of the fourth buffer bag B.23 is fluidly and sterilely connected to the at least one inlet of the fourth means for transferring fluid AS3.

According to said embodiment, the method further comprises the following steps:
  applying acoustic field inside the channel of the fourth means for transferring fluid AS3 by means of the acoustic wave generator;
  transferring the content of the fourth sampling bag B.22 and the fourth buffer bag B.23 in the fourth means for transferring fluid AS3; and
  collecting platelet concentrate in the seventh sampling bag B.32.

According to one embodiment, said steps of platelets concentration may be repeated as needed, preferably from 1 to 10 times.

According to one embodiment, the throughput of blood product preparation (i.e. the flow rate inside the means for transferring fluid AS0, AS1, AS2, AS3 is ranging from 0.5 mL/min to 100 mL/min, from 0.5 to 20 mL/min or about 20 mL/min.

According to one embodiment, the method for preparation of blood product is not an apheresis.

According to one embodiment, the transfer of the content of the bag(s) in the means for transferring fluid is performed in any appropriate manner, such as gravity flow or active flow system (e.g. pumps) located on the external side or surface of the closed disposable sterile multiple blood bag system.

This invention also relates to a multiple bag system for fractionating a biological fluid into its components. The present invention especially relates to a closed disposable sterile multiple blood bag system for fractionating blood a depicted in FIG. 2.

Said closed disposable multiple sterile blood bag system for fractionating blood comprises:
  a fluid collecting bag B.00 comprising at least one outlet port;
  first and second sampling bags B.10, B.12, each comprising at least one inlet port and at least one outlet port;
  first means for transferring fluid AS0 from the fluid collecting bag B.00 to the first and second sampling bags B.10, B.12;
wherein the first means for transferring fluid AS0 comprises:
  a channel extending along a longitudinal axis, the channel having a cross section with a width measured along a first transverse axis and a thickness measured along a second transverse axis (z) perpendicular to the first transverse axis, the width being greater than or equal to the thickness, the channel having first and second walls along the second transverse axis (z);
  at least one inlet in fluid communication with the channel;
  at least first and second outlets in fluid communication with the channel, the first outlet being separated, on the second transverse axis (z), from the second outlet;
  and
  at least one acoustic wave generator for generating acoustic wave having a wavelength $\lambda$ within the channel;

wherein the thickness of the channel is equal to $\lambda/2$; the at least one outlet port of the fluid collecting bag B.00 is fluidly and sterilely connected to the at least one inlet of the first means for transferring fluid AS0 and the at least first and second outlets of the first means for transferring fluid AS0 are fluidly and sterilely connected to the at least one inlet port of respectively the first and second sampling bags B.10, B.12.

According to one embodiment, the closed disposable multiple sterile blood bag system for fractionating blood further comprises a first buffer bag comprising at least one outlet port; said first buffer bag containing a buffer medium, and the at least one outlet port of the first buffer bag is fluidly and sterilely connected to the at least one inlet of the first means for transferring fluid AS0.

According to one embodiment, the fluid collecting bag B.00 comprises an inlet port which is fluidly and sterilely connected to a vein puncture needle.

According to one embodiment, the closed disposable sterile multiple blood bag system further comprises an initial sampling bag comprising an inlet port which is fluidly and sterilely connected to a vein puncture needle and an outlet port which is fluidly and sterilely connected to the fluid collecting bag B.00.

According to one embodiment, as depicted in FIG. 3, the closed disposable sterile multiple blood bag system further comprises:
  third and a fourth sampling bag B.20, B.22, each comprising at least one inlet port and at least one outlet port;
  a second buffer bag B.11 comprising at least one outlet port; said second buffer bag B.11 containing a buffer medium;
  second means for transferring fluid AS1 from the first sampling bag B.10 to the third and fourth sampling bags B.20, B.22; and
  wherein the second means for transferring fluid AS1 comprises:
    a channel extending along a longitudinal axis, the channel having a cross section with a width measured along a first transverse axis and a thickness measured along a second transverse axis (z) perpendicular to the first transverse axis, the width being greater than or equal to the thickness, the channel having first and second walls along the second transverse axis (z);

at least one inlet in fluid communication with the channel;

at least first and second outlets in fluid communication with the channel, the first outlet being separated, on the second transverse axis (z), from the second outlet; and at least one acoustic wave generator for generating acoustic wave having a wavelength λ within the channel;

wherein the thickness of the channel is equal to λ/2; the at least one outlet port of the first sampling bag B.10 is fluidly and sterilely connected to the at least one inlet of the second means for transferring fluid AS1, the at least first and second outlets of the second means for transferring fluid AS1 are fluidly and sterilely connected to the inlet port of respectively the third and fourth sampling bags B.20, B.22; and the outlet of the second buffer bag B.11 is fluidly and sterilely connected to the at least one inlet of the second means for transferring fluid AS1.

According to one embodiment, the closed disposable sterile multiple blood bag system further comprises:

fifth and sixth sampling bag B.30, B.31, each comprising at least one inlet port and at least one outlet port;

a third buffer bag B.21 comprising at least one outlet port; said third buffer bag B.21 containing a buffer medium;

third means for transferring fluid AS2 from the third sampling bag B.20 to the fifth and sixth sampling bags B.30, B.31; and wherein the third means for transferring fluid AS2 comprises:

a channel extending along a longitudinal axis, the channel having a cross section with a width measured along a first transverse axis and a thickness measured along a second transverse axis (z) perpendicular to the first transverse axis, the width being greater than or equal to the thickness, the channel having first and second walls along the second transverse axis (z);

at least one inlet in fluid communication with the channel;

at least first and second outlets in fluid communication with the channel, the first outlet being separated, on the second transverse axis (z), from the second outlet; and at least one acoustic wave generator for generating acoustic wave having a wavelength λ within the channel;

wherein the thickness of the channel is equal to λ/2; the at least one outlet port of the third sampling bag B.20 is fluidly and sterilely connected to the at least one inlet of the third means for transferring fluid AS2, the at least first and second outlets of the third means for transferring fluid AS2 are fluidly and sterilely connected to the inlet port of respectively the fifth and sixth sampling bags B.30, B.31; and the outlet of the third buffer bag B.21 is fluidly and sterilely connected to the at least one inlet of the third means for transferring fluid AS2.

According to one embodiment as depicted in FIG. 4, the closed disposable sterile multiple blood bag system further comprises:

seventh and eight sampling bag B.32, B.33, each comprising at least one inlet port and at least one outlet port;

a fourth buffer bag B.23 comprising at least one outlet port; said fourth buffer bag containing a buffer medium;

fourth means for transferring fluid AS3 from the fourth sampling bag B.22 to the seventh and eight sampling bag B.32, B.33; and wherein the fourth means for transferring fluid AS3 comprises:

a channel extending along a longitudinal axis, the channel having a cross section with a width measured along a first transverse axis and a thickness measured along a second transverse axis (z) perpendicular to the first transverse axis, the width being greater than or equal to the thickness, the channel having first and second walls along the second transverse axis (z);

at least one inlet in fluid communication with the channel;

at least first and second outlets in fluid communication with the channel, the first outlet being separated, on the second transverse axis (z), from the second outlet; and at least one acoustic wave generator for generating acoustic wave having a wavelength λ within the channel;

wherein the thickness of the channel is equal to λ/2; the at least one outlet port of the fourth sampling bag B.22 is fluidly and sterilely connected to the at least one inlet of the fourth means for transferring fluid AS3, the at least first and second outlets of the fourth means for transferring fluid AS3 are fluidly and sterilely connected to the inlet port of respectively the seventh and eight sampling bag B.32, B.33; the outlet of the fourth buffer bag B.23 is fluidly and sterilely connected to the at least one inlet of the fourth means for transferring fluid AS3.

According to one embodiment, the fluid collecting bag B.00 has a volume ranging from 250 mL to 1L, preferably from 350 to 530 mL.

According to one embodiment, the second sampling bag B.12 has a volume ranging from 200 mL to 750 mL, preferably about 280 mL.

According to one embodiment, the initial sampling bag has a volume of about 30 mL.

According to one embodiment, the seventh sampling bag B.32 has a volume ranging from 20 mL to 100 mL, preferably about 50 mL.

According to one embodiment, the third and/or fifth sampling bag B.20, B.30 have a volume ranging from 200 mL to 750 mL, preferably about 280 mL.

According to one embodiment, the buffer medium is an additive solution for preservation and/or for anticoagulation. According to one exemplary embodiment, the additive solution for preservation is selected from SAG-Mannitol (SAGM), PSA IIIm or SSP+. According to one exemplary embodiment, the additive solution for anticoagulation is a citrate-phosphate-dextrose solution (CPD).

According to one embodiment, as depicted in FIG. 9, the system comprises a fluid collecting bag B'.10, at least first and second sampling bags B'.20, B'.22, each bag B'.10, B'.20, B'.22 comprising at least one inlet port and at least one outlet port; means for transferring fluid AS'1 from the collecting bag B'.10 to the sampling bags B'.20, B'.22, and a first bag comprising a buffer medium B'.11 comprising at least one outlet port.

Said means for transferring fluid AS'1, also called acoustic sorter, comprise:

a channel extending along a longitudinal axis, the channel having a cross section with a width measured along a first transverse axis and a thickness measured along a second transverse axis (z) perpendicular to the first transverse axis, the width being greater than or equal to the thickness, the channel having first and second walls along the second transverse axis (z);

at least first and second inlets in fluid communication with the channel, the first inlet being separated (i.e. spaced and distinct), on the second transverse axis (z), from the second inlet; and at least first and second outlets in fluid communication with the channel, the first outlet being separated (i.e. spaced and distinct), on the second transverse axis (z), from the second outlet.

According to one embodiment, the means for transferring fluid AS'1 comprises a single inlet in fluid communication with the channel.

According to one embodiment, the means for transferring fluid AS'1 further comprises at least one acoustic wave generator for generating acoustic wave having a wavelength $\lambda$ within the channel. In said embodiment, the thickness of the channel is equal to $\lambda/2$.

By applying an acoustic force field over the thickness and over the width of the channel, by means of an acoustic wave generator, it may be possible to move a set of particles depending of their sizes in any area of the channel, and thus to sort and fractionate a biological fluid.

As depicted in FIG. 9, the at least one outlet port of the collecting bag B'.10 is fluidly and sterilely connected to at least one of the inlet of the means for transferring fluid AS'1; the at least first and second outlets of the means for transferring fluid AS'1 are fluidly and sterilely connected to the at least one inlet port of respectively the first and second sampling bags B'.20, B'.22; and the at least one outlet port of the first bag comprising a buffer medium B'.11 is fluidly and sterilely connected to at least one of the inlets of the means for transferring fluid AS'1.

According to one embodiment, the at least one outlet port of the collecting bag B'.10 is fluidly and sterilely connected to the at least one outlet port of the first bag comprising a buffer medium B'.11 upstream of the single inlet of the means for transferring fluid AS'1.

According to one embodiment, the fluid connections between the transferring means and the bags comprise any means known by one skilled in the art, such as flexible manifolds or tubes and clamps or valves. Their representations in the drawings are not representative in dimensions and positions.

According to one embodiment, the biological fluid is whole blood and the multiple bag system allows fractionating of blood products such as RBC, WBC, PC and blood plasma, such as PPP or PRP, without centrifugation.

According to one embodiment, the fluid collecting bag B'.10 is a blood collecting bag for collecting the whole blood, the first sampling bag B'.20 is a red blood cell, white blood cell and buffer storing bag and the second sampling bag B'.22 is a plasma storing bag such as a platelet rich plasma storing bag. According to one embodiment, the fluid collecting bag B'.10 has a volume ranging from 500 mL to 1L, preferably about 700 mL.

According to another embodiment, the multiple bag system of the invention is used to separate the plasma from the blood cells (plasmapheresis). According to said embodiment, the fluid collecting bag B'.10 is a blood collecting bag for collecting the whole blood, the first sampling bag B'.20 is a blood cell storing bag and the second sampling bag B'.22 is a blood plasma storing bag.

According to one embodiment, the inlet port of the blood collecting bag B'.10 is fluidly and sterilely connected to a vein puncture needle.

According to one embodiment, the multiple bag system further comprises a third and a fourth sampling bag B'.30, B'.31, each comprising at least one inlet port and at least one outlet port; second means for transferring fluid AS'2 from the first sampling bag B'.20 to the third and fourth sampling bags B'.30, B'.31 and a second bag comprising a buffer medium B'.21 comprising at least one outlet port. Within said extended system, the at least one outlet port of the first sampling bag B'.20 is fluidly and sterilely connected to at least one of the inlets of the second means for transferring fluid AS'2 the at least first and second outlets of the second means for transferring fluid AS'2 are fluidly and sterilely connected to the inlet port of respectively the third and fourth sampling bags B'.30, B'.31; and the outlet of the second bag comprising a buffer medium B'.21 is fluidly and sterilely connected to at least one of the inlets of the second means for transferring fluid AS'2.

According to one embodiment, the at least one outlet port of the first sampling bag B'.20 is fluidly and sterilely connected to the at least one outlet port of the second bag comprising a buffer medium B'.21 upstream of the single inlet of the second means for transferring fluid AS'2.

According to one embodiment, the multiple bag system further comprises a fifth and a sixth sampling bag B'.32, B'.33, each comprising at least one inlet port and at least one outlet port; third means for transferring fluid AS'3 from the second sampling bag B'.22 to the fifth and sixth sampling bags B'.32, B'.33, and a third bag comprising a buffer medium B'.23 comprising at least one outlet port. Within said extended system, the at least one outlet port of the second sampling bag B'.22 is fluidly and sterilely connected to at least one of the inlets of the third means for transferring fluid AS'3, the at least first and second outlets of the third means for transferring fluid AS'3 are fluidly and sterilely connected to the inlet port of respectively the fifth and sixth sampling bags B'.32, B'.33; and the outlet of the third bag comprising a buffer medium B'.23 is fluidly and sterilely connected to at least one of the inlets of the third means for transferring fluid AS'3.

According to one embodiment, the at least one outlet port of the first sampling bag B'.22 is fluidly and sterilely connected to the at least one outlet port of the third bag comprising a buffer medium B'.23 upstream of the single inlet of the third means for transferring fluid AS'3.

According to one embodiment, as depicted in FIG. 10, the multiple bag system further comprises a third, a fourth, a fifth and a sixth sampling bag B'.30, B'.31, B'.32, B'.33, each comprising at least one inlet port and at least one outlet port; second means for transferring fluid AS'2 from the first sampling bag B'.20 to the third and fourth sampling bags B'.30, B'.31, third means for transferring fluid AS'3 from the second sampling bag B'.22 to the fifth and sixth sampling bags B'.32, B'.33, and a second and a third bag comprising a buffer medium B'.21, B'.23, each comprising at least one outlet port. Within said extended system, the at least one outlet port of the first sampling bag B'.20 is fluidly and sterilely connected to at least one of the inlets of the second means for transferring fluid AS'2, the at least first and second outlets of the second means for transferring fluid AS'2 are fluidly and sterilely connected to the inlet port of respectively the third and fourth sampling bags B'.30, B'.31, the outlet of the second bag comprising a buffer medium B'.21 is fluidly and sterilely connected to at least one of the inlets of the second means for transferring fluid AS'2, the at least one outlet port of the second sampling bag B'.22 is fluidly and sterilely connected to at least one of the inlets of the third means for transferring fluid AS'3, the at least first and second outlets of the third means for transferring fluid AS'3 are fluidly and sterilely connected to the inlet port of respectively the fifth and sixth sampling bags B'.32, B'.33; and the outlet of the third bag comprising a buffer medium B'.23 is fluidly and sterilely connected to at least one of the inlets of the third means for transferring fluid AS'3.

According to one embodiment as depicted in FIG. 11, the means for transferring fluid AS'1 comprises a single inlet in fluid communication with the channel and the at least one outlet port of the collecting bag B'.10 is fluidly and sterilely connected to the at least one outlet port of the first bag comprising a buffer medium B'.11 upstream of the single inlet of the means for transferring fluid AS'1.

According to one embodiment, the third sampling bag B'.30 is a red blood cell storing bag and the fourth sampling bag B'.31 is a white blood cell storing bag. According to one embodiment, the fifth sampling bag B'.32 is a plasma storing bag and the sixth sampling bag B'.33 is a platelet concentrated storing bag.

According to one embodiment, the first, second and third bags comprising a buffer medium B'.11, B'.21, B'.23 comprise any buffer medium known by one skilled in the art. Especially, B'.11 and B'.21 may comprise anticoagulant such as for instance citrate-phosphate-dextrose solution (CPD) and/or additive solution for preservation such as SAG-Mannitol (SAGM), PSA IIIm or SSP+; and B'.23 may comprise a preservative medium, such as for instance SAG-Mannitol (SAGM), PSA IIIm or SSP+PAS IIIm.

According to one embodiment, the second and third means for transferring fluid AS'2, AS'3 comprise:
  a channel extending along a longitudinal axis, the channel having a cross section with a width measured along a first transverse axis and a thickness measured along a second transverse axis (z) perpendicular to the first transverse axis, the width being greater than or equal to the thickness, the channel having first and second walls along the second transverse axis (z);
  at least first and second inlets in fluid communication with the channel, the first inlet being separated, on the second transverse axis (z), from the second inlet; and
  at least first and second outlets in fluid communication with the channel, the first outlet being separated, on the second transverse axis (z), from the second outlet.

According to one embodiment, the means for transferring fluid AS0, AS1, AS2, AS3, AS'1, AS'2, AS'3 (also referred to as acoustic sorters) are identical. According to one embodiment, the means for transferring fluid AS0, AS1, AS2, AS3, AS'1, AS'2, AS'3 are not identical.

According to one embodiment, the means for transferring fluid AS0, AS1, AS2, AS3, AS'1, AS'2, AS'3 comprises at least first and second inlets in fluid communication with the channel, the first inlet being separated, on the second transverse axis (z), from the second inlet.

According to one embodiment, one or more of the means for transferring fluid AS0, AS1, AS2, AS3, AS'1, AS'2, AS'3 further comprises at least a first transverse separation wall separating the first and second inlets.

According to one embodiment, at least one of the inlets of the means for transferring fluid AS0, AS1, AS2, AS3, AS'1, AS'2, AS'3 has a width equal to the width of the channel. According to one embodiment, one or more of the means for transferring fluid AS0, AS1, AS2, AS3, AS'1, AS'2, AS'3 further comprises at least a third inlet in fluid communication with the channel, the second inlet being disposed on the second transverse axis (z) between the first and third inlets.

According to one embodiment, one or more of the means for transferring fluid AS0, AS1, AS2, AS3, AS'1, AS'2, AS'3 further comprises at least a third outlet in fluid communication with the channel, the second outlet being disposed on the second transverse axis (z) between the first and third outlets.

According to one embodiment wherein the means for transferring fluid AS0, AS1, AS2, AS3, AS'1, AS'2, AS'3 comprises at least three inlets, one or more of the means for transferring fluid AS0, AS1, AS2, AS3, AS'1, AS'2, AS'3 further comprises first and second transverse separation walls respectively separating the first and second inlets and the second and third inlets, the first and second separation walls being arranged in such a manner that the second inlet is separated from each of said bottom and top walls by a non-zero distance measured along the second transverse axis (z). Said embodiment, depicted in FIG. 5, enables decoupling the second inlet from the first and third inlets.

According to one embodiment, as depicted in FIGS. 6 and 7, the first, second and third inlets i1, i2, i3 of one or more of the means for transferring fluid AS0, AS1, AS2, AS3, AS'1, AS'2, AS'3 open out in the first or second walls of the channel perpendicularly to the longitudinal axis. According to one embodiment, as depicted in FIGS. 6 and 7, the first and third inlets i1, i3 of one or more of the means for transferring fluid AS0, AS1, AS2, AS3, AS'1, AS'2, AS'3 open out respectively in the top and bottom walls of the channel, perpendicularly to the longitudinal axis and facing each other.

According to one embodiment, as depicted in FIG. 5, the first, second and third inlets i2, i3 of one or more of the means for transferring fluid AS0, AS1, AS2, AS3, AS'1, AS'2, AS'3 open out in the channel parallel to the longitudinal axis.

According to one embodiment, the inlets and the outlets of the means for transferring fluid AS0, AS1, AS2, AS3, AS'1, AS'2, AS'3 are symmetrical.

According to one embodiment, each inlet creates its own fluid layer in the channel and the fluid layers do not mix unless acoustic waves are applied. The use of acoustic force fields for handling object is described for instance in US patent application US 2014/0230912. By applying an acoustic force field over the thickness and over the width, it may be possible to move a set of particles depending of their sizes in any area of the channel, and thus to sort and fractionate biological fluid. According to one embodiment, as depicted in FIGS. 5 to 7, the upper and lower fluid layers h1, h3 within the channel have a height ranging from 0.05 mm to 0.3 mm and the middle fluid layer h2 has a height ranging from 0.1 mm to 0.8 mm.

According to one embodiment wherein the first means for transferring fluid AS0 comprises at least three inlets i1, i2, i3, the at least one outlet port of the fluid collecting bag B.00 is fluidly and sterilely connected to the first and third inlets i1, i3 of the first means for transferring fluid AS0 and the at least one outlet port of the first buffer bag comprising a buffer medium is fluidly and sterilely connected to the second inlet i2 of the first means for transferring fluid AS0.

According to one embodiment wherein the first means for transferring fluid AS0 comprises at least three outlets o1, o2, o3, the second outlet o2 of the first means for transferring fluid AS0 is fluidly and sterilely connected to the inlet port of the first sampling bag B.10 and the first and third outlets o1, o3 of the first means for transferring fluid AS0 are fluidly and sterilely connected to the inlet port of the second sampling bag B.12.

According to one embodiment wherein the second means for transferring fluid AS1 comprises at least three inlets i1, i2, i3, the at least one outlet port of the first sampling bag B.10 is fluidly connected to the first and third inlets i1, i3 of the second means for transferring fluid AS1 and the at least one outlet port of the second buffer bag B.11 comprising a buffer medium is fluidly connected to the second inlet i2 of the second means for transferring fluid AS1.

According to one embodiment wherein the second means for transferring fluid AS1 comprises at least three outlets o1, o2, o3, the second outlet o2 of the second means for transferring fluid AS1 is fluidly and sterilely connected to the inlet port of the fourth sampling bag B.22 and the first and third outlets o1, o3 of the second means for transferring fluid AS1 are fluidly connected to the inlet port of the third sampling bag B.20.

According to one embodiment wherein the third means for transferring fluid AS2 comprises at least three inlets i1, i2, i3, the at least one outlet port of the third sampling bag B.20 is fluidly and sterilely connected to the first and third inlets i1, i3 of the third means for transferring fluid AS2 and the at least one outlet port of the third buffer bag B.21 comprising a buffer medium is fluidly and sterilely connected to the second inlet i2 of the third means for transferring fluid AS2.

According to one embodiment wherein the third means for transferring fluid AS2 comprises at least three outlets o1, o2, o3, the second outlet o2 of the third means for transferring fluid AS2 is fluidly and sterilely connected to the inlet port of the sixth sampling bag B.31 and the first and third outlets o1, o3 of the third means for transferring fluid AS2 are fluidly and sterilely connected to the inlet port of the fifth sampling bag B.30.

According to one embodiment wherein the fourth means for transferring fluid AS3 comprises at least three inlets i1, i2, i3, the at least one outlet port of the fourth sampling bag B.22 is fluidly and sterilely connected to the first and third inlets i1, i3 of the fourth means for transferring fluid AS3 and the at least one outlet port of the fourth buffer bag B.23 comprising a buffer medium is fluidly and sterilely connected to the second inlet i2 of the fourth means for transferring fluid AS3.

According to one embodiment wherein the fourth means for transferring fluid AS3 comprises at least three outlets o1, o2, o3, the second outlet o2 of the fourth means for transferring fluid AS0 is fluidly connected to the inlet port of the first sampling bag B.10 and the first and third outlets o1, o3 of the fourth means for transferring fluid AS3 are fluidly connected to the inlet port of the second sampling bag B.12.

According to one embodiment, as depicted in FIG. 7, the first and second walls of the channel along the second transverse axis (z) are a transmitter or carrier layer and a reflector layer.

According to one embodiment, the reflector layer is made from a metal, preferably titanium or stainless steel.

According to one embodiment, the means for transferring fluid AS0, AS1, AS2, AS3, AS'1, AS'2, AS'3, especially the first and second walls, is made from a material chosen among mineral or organic glasses, quartz, thermoplastic materials such as PMMA or polycarbonate, and metals.

According to one embodiment, the channel has a thickness ranging from 0.2 mm to 2 mm, preferably about 0.750 mm, a width ranging from 2 mm to 20 mm and a length ranging from 10 mm to 200 mm. According to one embodiment, the channel has a thickness higher than 300 micrometers, preferably ranging from 375 micrometers to 750 micrometers.

According to one embodiment, the channel has a length, measured along the longitudinal axis ranging from 3 mm to 20 cm, preferably from 3 mm to 10 cm, more preferably from 10 mm to 70 mm. According to one embodiment, the channel has a length, measured along the longitudinal axis higher than 10 centimeters.

According to one embodiment, the channel has a width higher than 10 millimeters.

According to one embodiment, the channel has a substantially rectangular cross-section along at least a portion of its length. According to one embodiment, the width/thickness ratio of the channel is greater than 2. According to one embodiment, the length/thickness ratio of the channel is greater than 10.

According to one embodiment, the thickness and the width of the channel are constant along the longitudinal axis. According to one embodiment, the thickness and the width of the channel are variable along the longitudinal axis.

According to one embodiment, the carrier layer has a thickness ranging from 0.2 mm to 2 mm, preferably about 1 mm.

According to one embodiment, the reflector layer has a thickness ranging from 0.2 mm to 2 mm, preferably about 0.5 mm.

As well known to one skilled in the art of acoustophoresis, the thickness of the reflector layer may be half the thickness of the carrier layer or the thickness of the reflector layer may be equal to the thickness of the carrier layer.

According to one embodiment, as shown in FIGS. 7 and 8, one or more of the means for transferring fluid AS0, AS1, AS2, AS3, AS'1, AS'2, AS'3 further comprise at least one acoustic wave generator which generates acoustic waves in the channel from at least one of the walls. According to one embodiment, one or more of the means for transferring fluid AS0, AS1, AS2, AS3, AS'1, AS'2, AS'3 comprises a plurality of acoustic wave generators arranges along the channel; said plurality of acoustic wave generators being preferably positioned on the same side of the channel. According to one embodiment, the acoustic waves are generated at a frequency ranging from 0.5 MHz to 10 MHz, preferably about 1 MHz.

According to one embodiment, the at least one acoustic wave generator is configured for generating acoustic wave having a wavelength λ within the channel. In said embodiment, the thickness of the channel is equal to $$\frac{\lambda}{2},$$

or the thickness of the channel is equal to a multiple of $$\frac{\lambda}{2}.$$

According to one embodiment, the acoustic wave generator is configured for generating volumetric acoustic standing waves. According to one embodiment, the acoustic wave generator is not configured for generating surface acoustic waves.

According to one embodiment, as depicted in FIG. 8, the acoustic wave generator or transducer is pressed on one of the walls of the means for transferring fluid AS0, AS1, AS2, AS3, AS'1, AS'2, AS'3. According to said embodiment, a proper medium such as for instance ultrasonic gel is positioned between the transducer and the wall to ensure good transmission of the acoustic waves.

According to one alternative embodiment, as depicted in FIG. 7, the acoustic wave generator or transducer is integrated within one of the walls, such as for instance by bonding or any other means known by one skilled in the art.

According to one embodiment, the at least one acoustic wave generator is coupled to the first wall by a dry acoustic coupling. In said embodiment, the first wall is the transmitter or carrier layer and the second wall is the reflector layer.

According to one embodiment, the at least one acoustic wave generator is coupled to the first wall (i.e. the transmitter or carrier layer) with a coupling layer. According to one embodiment, said coupling layer.

According to one embodiment, said coupling layer is made from thermoplastic elastomers, thermoplastic polyurethanes or silicone. According to one embodiment, said coupling layer has a hardness ranging from 5 to 50 Shore A. According to one embodiment, the attenuation within the coupling layer is ranging from 0 to 1 dB/mm. According to one embodiment, the attenuation at the dry interface is lower than 8 dB (compared to the attenuation with a gel acoustic coupling). According to one embodiment, the contact pressure at the dry interface is ranging from 12 to 60 kPa.

According to one exemplary embodiment, the coupling layer is made from Aqualene® commercialized by OLYMPUS.

According to one embodiment, the acoustic conductance coefficient of the first wall (i.e. the transmitter or carrier layer) is ranging from 0.5 to 1, preferably from 0.75 to 1, more preferably from 0.9 to 1. According to one embodiment, the first wall (i.e. the transmitter or carrier layer) is made from a material exhibiting an acoustic conductance coefficient ranging from 0.5 to 1, preferably from 0.75 to 1, more preferably from 0.9 to 1.

According to one embodiment, the acoustic reflection coefficient of the second wall (i.e. the reflector layer) is ranging from 0.5 to 1, preferably from 0.75 to 1, more preferably from 0.9 to 1. According to one embodiment, the second wall (i.e. the reflector layer) is made from a material exhibiting an acoustic reflection coefficient ranging from 0.5 to 1, preferably from 0.75 to 1, more preferably from 0.9 to 1.

According to one embodiment, the closed disposable sterile multiple blood bag system further comprises at least one bag with additives solution.

According to one embodiment, the closed disposable sterile multiple blood bag system does not comprise active flow system, such as pumps or flow restrictors.

According to one embodiment, the closed disposable sterile multiple blood bag system does not comprise electrical connections.

According to one embodiment, the closed disposable sterile multiple blood bag system does not comprise a piezoelectric substrate.

According to one embodiment, the closed disposable sterile multiple blood bag system is not a washing system.

According to one embodiment, the channels of the means for transferring fluid are acoustic resonators. According to one embodiment, the channels of the means for transferring fluid are not one quarter wave separation chambers.

Figures 1A, 1B:
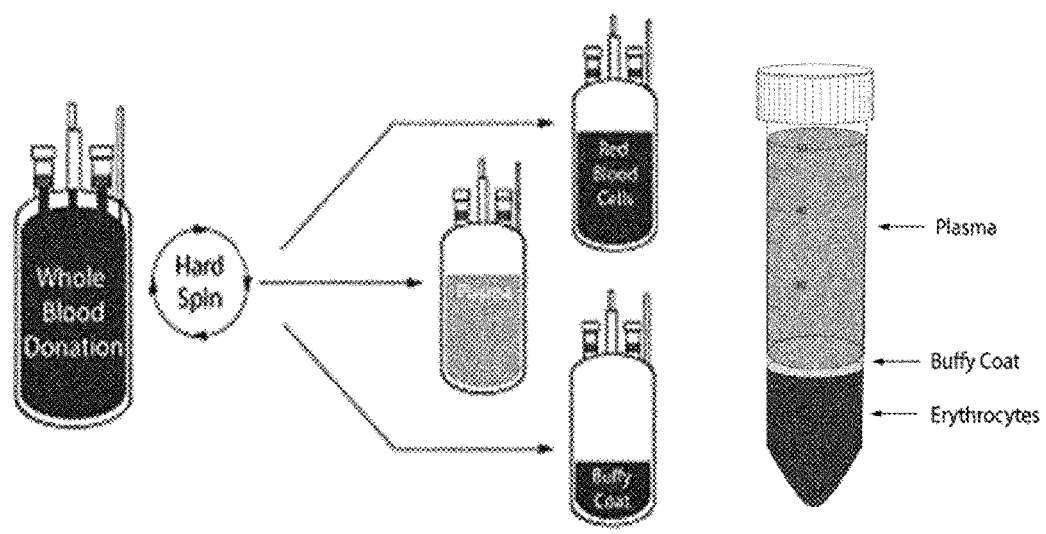
FIG. 1A shows the principles of production of various blood products using centrifugation according to the prior art.
FIG. 1B illustrates the stratification of various blood products after centrifugation of whole blood according to the prior art.
Figure 2:
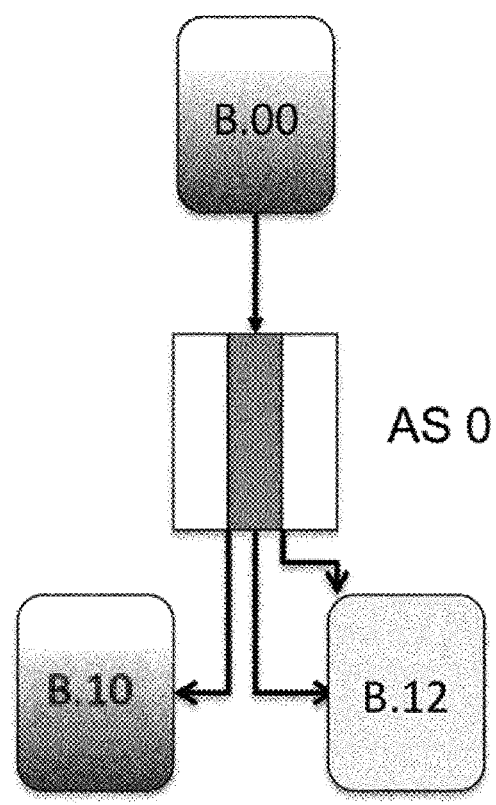
FIGS. 2, 3 and 4 depict a multiple blood bag system according to various embodiments of the invention.
Figure 3:
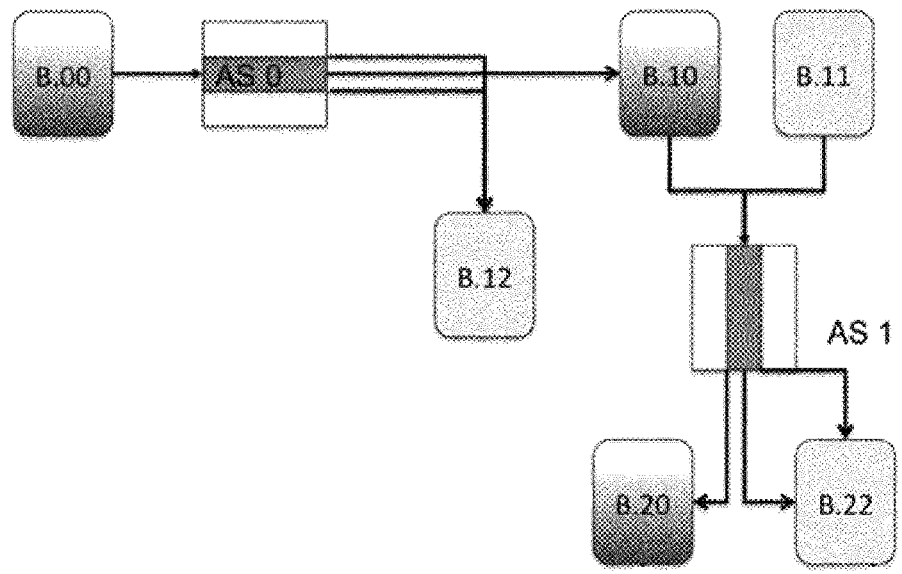
Figure 4:
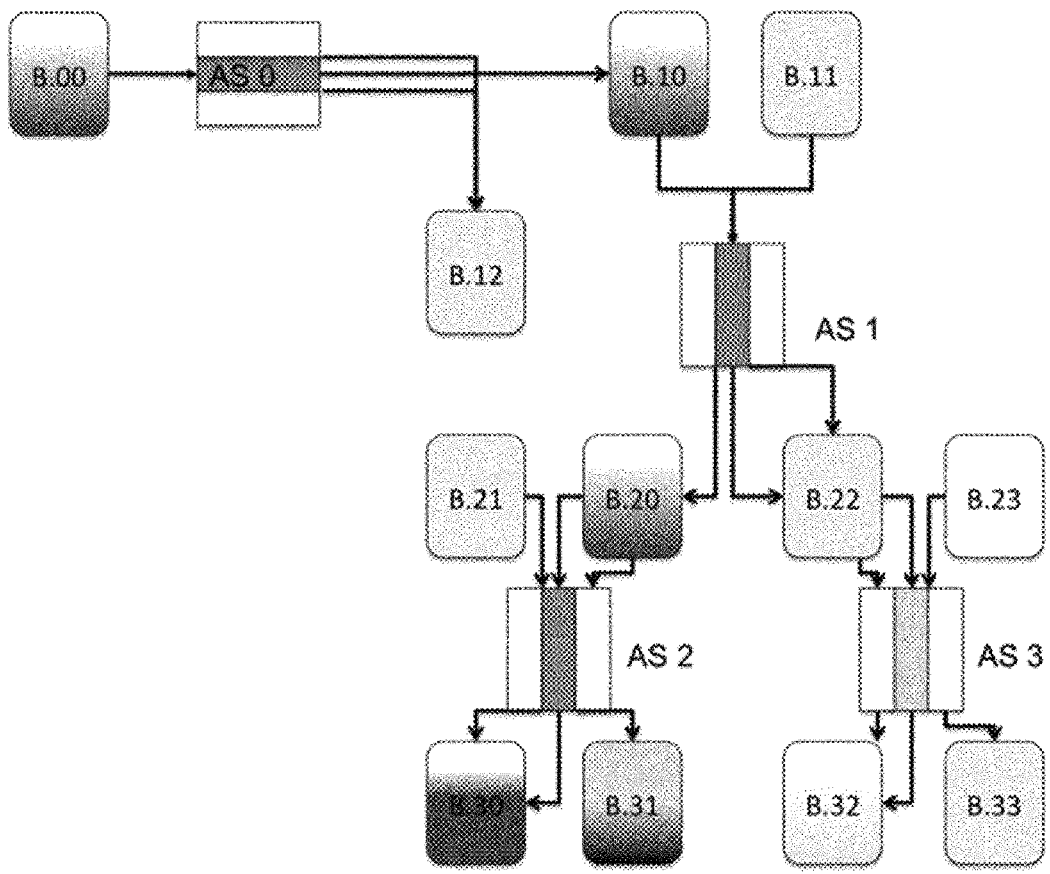
Figure 5:
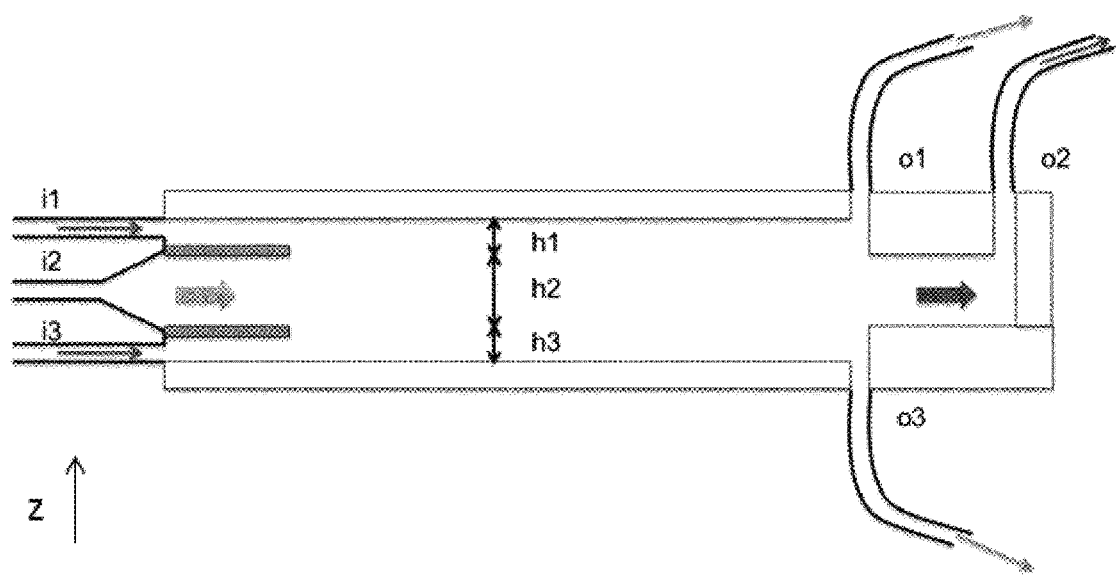
FIGS. 5 and 6 illustrate side-view of an acoustic sorter according to various embodiments of the invention.
Figure 6:
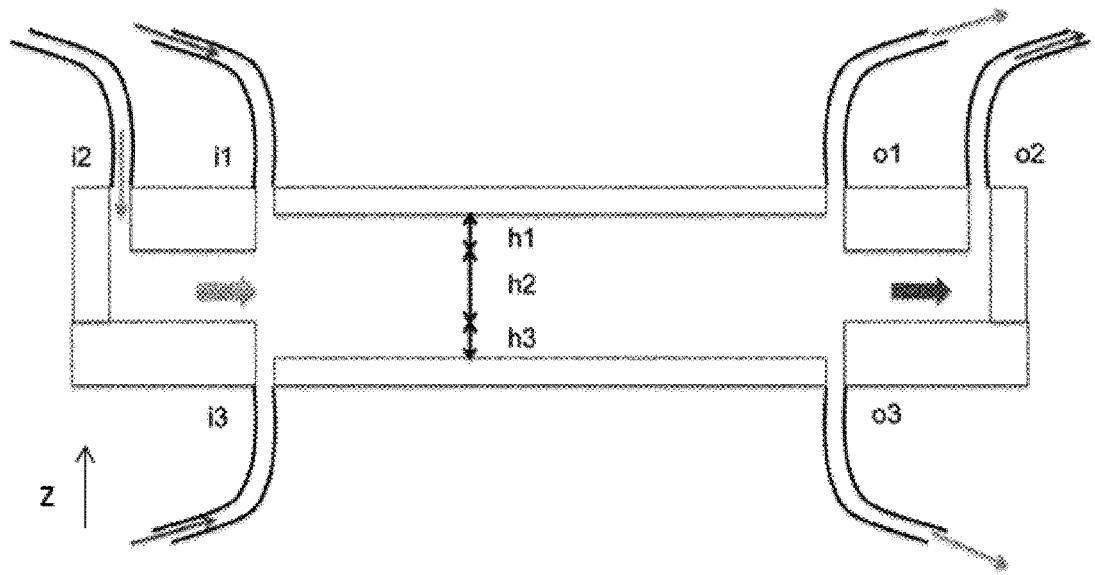
Figure 7:
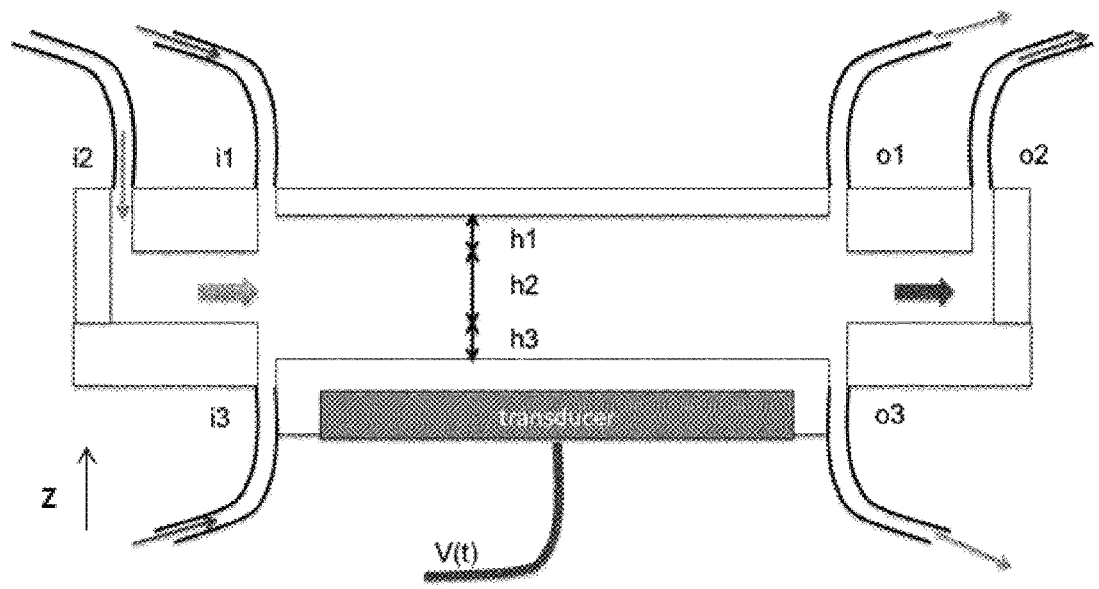
FIG. 7 is a side-view of an acoustic sorter according to one embodiment of the invention further comprising an integrated transducer.
Figure 8:
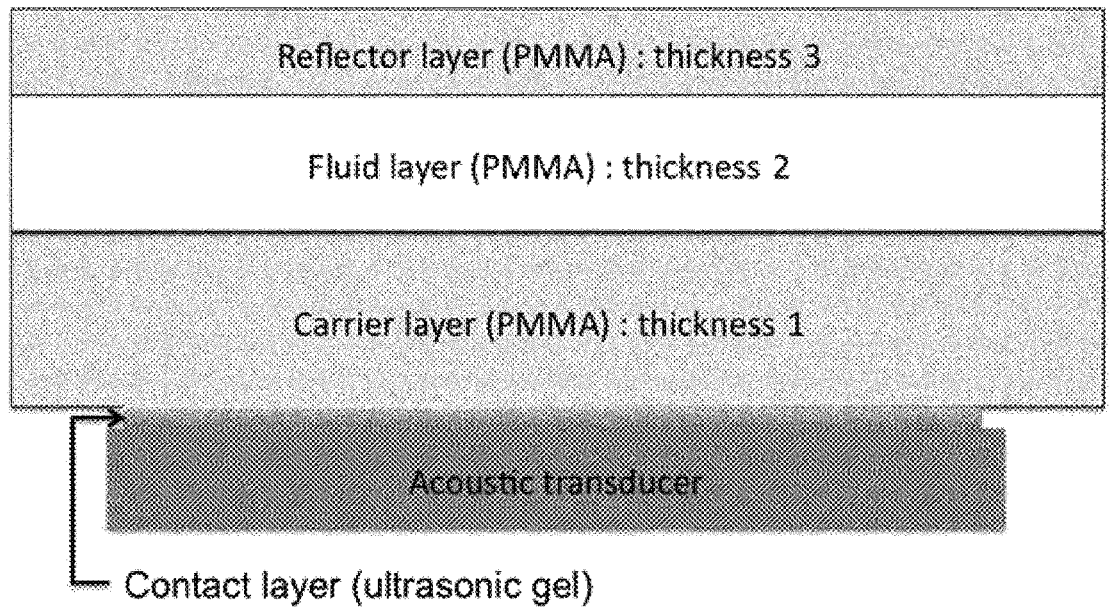
FIG. 8 depicts the multiples layer of an acoustic sorter according to one embodiment of the invention.
Figure 9:
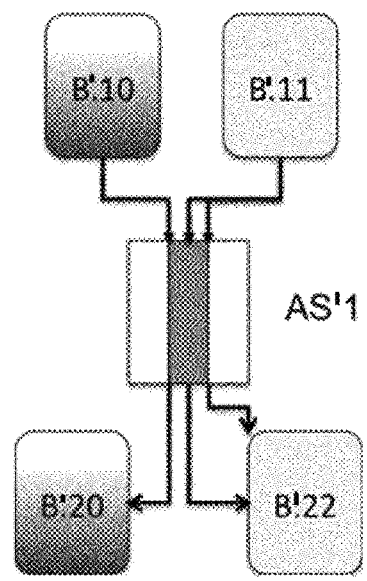
FIGS. 9, 10 and 11 illustrate a multiple blood bag system according to various embodiments of the present invention.
Figure 10:
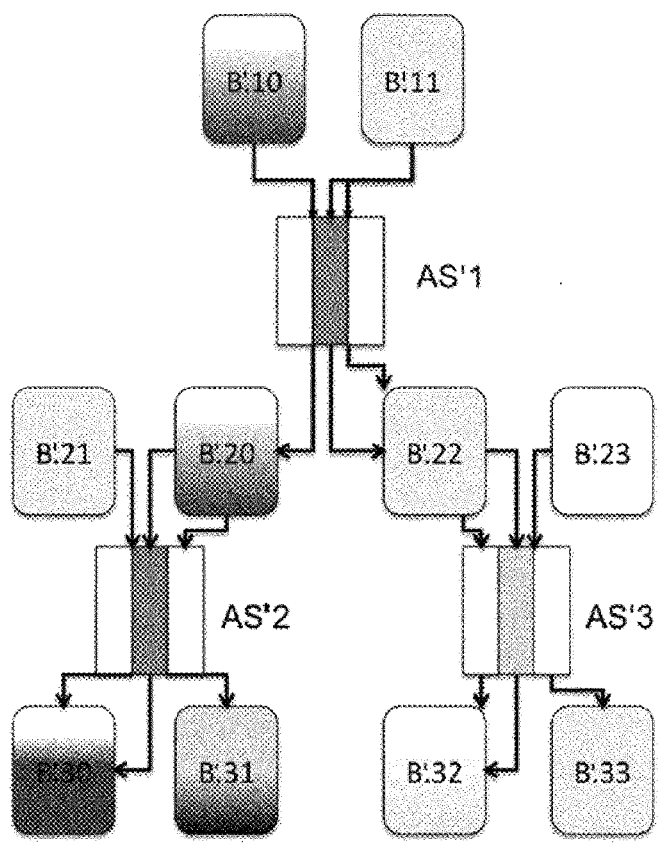
Figure 11:
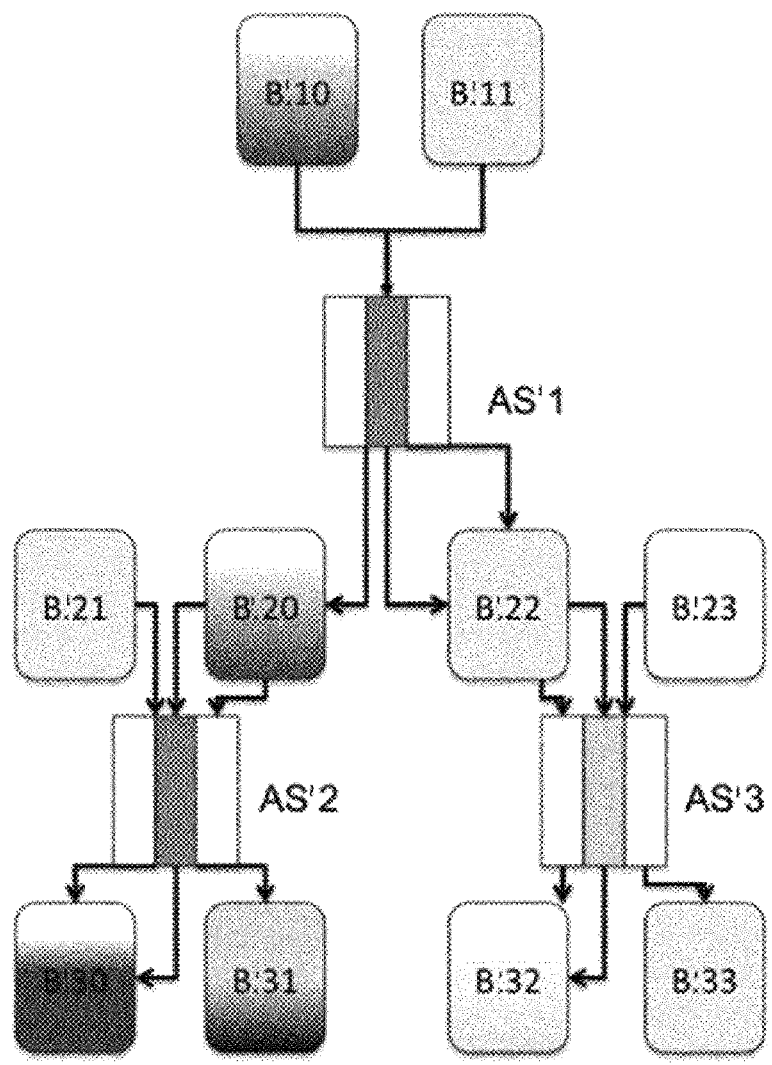

The invention claimed is:

1. A closed disposable multiple sterile blood bag system for fractionating blood, said system comprising:
   a fluid collecting bag comprising at least one outlet port;
   first and second sampling bags, each comprising at least one inlet port and at least one outlet port;
   first means for transferring fluid from the fluid collecting bag to the first and second sampling bags;
   wherein the first means for transferring fluid comprises:
      a channel extending along a longitudinal axis, the channel having a cross section with a width measured along a first transverse axis and a thickness measured along a second transverse axis perpendicular to the first transverse axis, the width being greater than or equal to the thickness, the channel having first and second walls along the second transverse axis, at least one wall being arranged for receiving an acoustic wave generator, said thickness of channel and said acoustic wave generator being intended to cooperate in order to generate a volumetric standing wave over the thickness of the channel for sorting and fractionating a fluid;
      at least one inlet in fluid communication with the channel;
      at least first and second outlets in fluid communication with the channel, the first outlet being separated, on the second transverse axis, from the second outlet; and
   the at least one outlet port of the fluid collecting bag is fluidly and sterilely connected to the at least one inlet of the first means for transferring fluid and the at least first and second outlets of the first means for transferring fluid are fluidly and sterilely connected to the at least one inlet port of respectively the first and second sampling bags.

2. A closed disposable multiple sterile blood bag system for fractionating blood according to claim 1, further comprising a first buffer bag comprising at least one outlet port; said first buffer bag containing a buffer medium, and the at least one outlet port of the first buffer bag is fluidly and sterilely connected to the at least one inlet of the first means for transferring fluid.

3. The closed disposable sterile multiple blood bag system according to claim 1, further comprising:
   third and a fourth sampling bags, each comprising at least one inlet port and at least one outlet port;
   a second buffer bag comprising at least one outlet port; said second buffer bag containing a buffer medium;
   second means for transferring fluid from the first sampling bag to the third and fourth sampling bags; and
   wherein the second means for transferring fluid comprises:
      a channel extending along a longitudinal axis, the channel having a cross section with a width measured along a first transverse axis and a thickness measured along a second transverse axis perpendicular to the first transverse axis, the width being greater than or equal to the thickness, the channel having first and second walls along the second transverse axis, at least one wall being arranged for receiving an acoustic wave generator, said thickness of channel and said acoustic wave generator being intended to cooperate in order to generate an acoustic force field over the thickness of the channel for sorting and fractionating a fluid;

at least one inlet in fluid communication with the channel;

at least first and second outlets in fluid communication with the channel, the first outlet being separated, on the second transverse axis, from the second outlet; and the at least one outlet port of the first sampling bag is fluidly and sterilely connected to the at least one inlet of the second means for transferring fluid, the at least first and second outlets of the second means for transferring fluid are fluidly and sterilely connected to the inlet port of respectively the third and fourth sampling bags; and the outlet of the second buffer bag is fluidly and sterilely connected to the at least one inlet of the second means for transferring fluid.

4. The closed disposable sterile multiple blood bag system according to claim 3, further comprising:

fifth and sixth sampling bags, each comprising at least one inlet port and at least one outlet port;

a third buffer bag comprising at least one outlet port;

said third buffer bag containing a buffer medium;

third means for transferring fluid from the third sampling bag to the fifth and sixth sampling bags; and wherein the third means for transferring fluid comprises:

a channel extending along a longitudinal axis, the channel having a cross section with a width measured along a first transverse axis and a thickness measured along a second transverse axis perpendicular to the first transverse axis, the width being greater than or equal to the thickness, the channel having first and second walls along the second transverse axis, at least one wall being arranged for receiving an acoustic wave generator, said thickness of channel and said acoustic wave generator being intended to cooperate in order to generate an acoustic force field over the thickness of the channel for sorting and fractionating a fluid;

at least one inlet in fluid communication with the channel;

at least first and second outlets in fluid communication with the channel, the first outlet being separated, on the second transverse axis, from the second outlet; and the at least one outlet port of the third sampling bag is fluidly and sterilely connected to the at least one inlet of the third means for transferring fluid, the at least first and second outlets of the third means for transferring fluid are fluidly and sterilely connected to the inlet port of respectively the fifth and sixth sampling bags; and the outlet of the third buffer bag (B.21) is fluidly and sterilely connected to the at least one inlet of the third means for transferring fluid.

5. The closed disposable sterile multiple blood bag system according to claim 1, wherein the at least one means for transferring fluid further comprises at least one acoustic wave generator, said acoustic wave generator being coupled to the first wall of the channel for generating acoustic wave having a wavelength $\lambda$ within the channel.

6. The closed disposable sterile multiple blood bag system according to claim 5, wherein the thickness of the channel of the at least one means for transferring fluid is equal to $$\frac{\lambda}{2}$$

or is equal to a multiple of $$\frac{\lambda}{2}.$$

7. The closed disposable sterile multiple blood bag system according to claim 1, wherein the fluid collecting bag comprises an inlet port which is fluidly and sterilely connected to a vein puncture needle.

8. The closed disposable sterile multiple blood bag system according to claim 1, wherein the second wall of the channel is a reflector, and wherein the acoustic reflection coefficient of the second wall is ranging from 0.5 to 1.

9. A method for high throughput preparation of blood products to be used for blood transfusion, the method comprising the following steps:

providing a closed disposable sterile multiple blood bag system comprising:

a fluid collecting bag comprising at least one outlet port, said fluid collecting bag containing whole blood obtained from an individual;

first and second sampling bags, each comprising at least one inlet port and at least one outlet port;

first means for transferring fluid from the first collecting bag to the sampling bags, wherein the first means for transferring fluid comprises:

a channel extending along a longitudinal axis, the channel having a cross section with a width measured along a first transverse axis and a thickness measured along a second transverse axis perpendicular to the first transverse axis, the width being greater than or equal to the thickness, the channel having first and second walls along the second transverse axis;

at least one inlet in fluid communication with the channel; and at least first and second outlets in fluid communication with the channel, the first outlet being separated, on the second transverse axis, from the second outlet;

the at least one outlet port of the fluid collecting bag is sterilely and fluidly connected to the at least one inlet of the first means for transferring fluid and the at least first and second outlets of the first means for transferring fluid are sterilely and fluidly connected to the at least one inlet port of respectively the first and second sampling bags;

applying acoustic field inside the channel of the means for transferring fluid by means of an acoustic wave generator configured to generate an acoustic force field over the thickness of the channel for sorting and fractionating a fluid;

transferring the content of the fluid collecting bag in the first means for transferring fluid; and collecting blood cells in the first sampling bag and blood plasma in the second sampling bag, wherein the acoustic field generated inside the channel of the means for transferring fluid contains volumetric acoustic standing waves and not surface acoustic waves.

10. The method for high throughput preparation of blood products according to claim 9, wherein the closed disposable sterile multiple blood bag system further comprises a first buffer bag comprising at least one outlet port, said first buffer bag containing a buffer medium, and said at least one outlet port is sterilely and fluidly connected to the at least one inlet of the first means for transferring fluid.

11. The method for high throughput preparation of blood products according to claim 9, wherein:
the closed disposable sterile multiple blood bag system further comprises:
a second buffer bag comprising at least one outlet port; said second buffer bag containing a buffer medium;
third and fourth sampling bags, each comprising at least one inlet port and at least one outlet port;
second means for transferring fluid from the first sampling bag to the third and fourth sampling bags, wherein the second means for transferring fluid comprises:
a channel extending along a longitudinal axis, the channel having a cross section with a width measured along a first transverse axis and a thickness measured along a second transverse axis perpendicular to the first transverse axis, the width being greater than or equal to the thickness, the channel having first and second walls along the second transverse axis;
at least one inlet in fluid communication with the channel; and
at least first and second outlets in fluid communication with the channel, the first outlet being separated, on the second transverse axis, from the second outlet;
the at least one outlet port of the first sampling bag is fluidly and sterilely connected to the at least one inlet of the second means for transferring fluid, the at least first and second outlets of the second means for transferring fluid are fluidly and sterilely connected to the inlet port of respectively the third and fourth sampling bags, and the at least one outlet port of the second buffer bag is fluidly and sterilely connected to the at least one inlet of the second means for transferring fluid; and
wherein the method further comprises the following steps:
applying acoustic field inside the channel of the second means for transferring fluid by means of an acoustic wave generator, configured to generate an acoustic force field over the thickness of the channel for sorting and fractionating a fluid;
transferring the content of the first sampling bag and the second buffer bag in the second means for transferring fluid; and
collecting red blood cell concentrate in the third sampling bag and platelet concentrate in the fourth collecting bag.

12. The method for high throughput preparation of blood products according to claim 11, wherein
the closed disposable sterile multiple blood bag system further comprises:
a third buffer bag comprising at least one outlet port; said third buffer bag containing a buffer medium;
fifth and sixth sampling bags, each comprising at least one inlet port and at least one outlet port;
third means for transferring fluid from the third sampling bag to the fifth and sixth sampling bags, wherein the third means for transferring fluid comprises:
a channel extending along a longitudinal axis, the channel having a cross section with a width measured along a first transverse axis and a thickness measured along a second transverse axis perpendicular to the first transverse axis, the width being greater than or equal to the thickness, the channel having first and second walls along the second transverse axis;
at least one inlet in fluid communication with the channel; and
at least first and second outlets in fluid communication with the channel, the first outlet being separated, on the second transverse axis, from the second outlet;
the at least one outlet port of the third sampling bag is fluidly and sterilely connected to the at least one inlet of the third means for transferring fluid, the at least first and second outlets of the third means for transferring fluid are fluidly and sterilely connected to the inlet port of respectively the fifth and sixth sampling bags, and the outlet of the third buffer bag is fluidly and sterilely connected to the at least one inlet of the third means for transferring fluid; and
wherein the method further comprises the following steps:
applying acoustic field inside the channel of the third means for transferring fluid by means of an acoustic wave generator configured to generate an acoustic force field over the thickness of the channel for sorting and fractionating a fluid;
transferring the content of the third sampling bag and the third buffer bag in the third means for transferring fluid; and
collecting red blood cell concentrate in the fifth sampling bag and white blood cell concentrate in the sixth collecting bag.

13. The method for high throughput preparation of blood products according to claim 9, wherein the acoustic wave generator is configured to generate acoustic wave having a wavelength $\lambda$ within the channel; and further wherein the thickness of the channel of one of at least one means for transferring fluid is equal to $$\frac{\lambda}{2}$$

or is equal to a multiple of $$\frac{\lambda}{2}.$$

14. The method for high throughput preparation of blood products according to claim 9, wherein the throughput is ranging from 0.5 mL/min to 100 mL/min.

* * * * *